United States Patent [19]

Suzuki

[11] Patent Number: 5,472,982
[45] Date of Patent: Dec. 5, 1995

[54] EMULSIFIED EXTERNAL TREATMENT COMPOSITION CONTAINING DICLOFENAC SODIUM

[75] Inventor: Takashi Suzuki, Yokohama, Japan

[73] Assignee: Shiseido Company Ltd., Tokyo, Japan

[21] Appl. No.: 175,480

[22] Filed: Dec. 29, 1993

Related U.S. Application Data

[63] Continuation of Ser. No. 875,573, Apr. 27, 1992, abandoned, which is a continuation of Ser. No. 731,376, Jul. 16, 1991, abandoned, which is a continuation of Ser. No. 384,238, Jul. 21, 1989, abandoned.

[30] Foreign Application Priority Data

Jul. 7, 1987 [JP] Japan .................................. 62-169565

[51] Int. Cl.⁶ .................................................. A61K 31/195
[52] U.S. Cl. .......................... 514/567; 514/785; 514/943
[58] Field of Search .................................. 514/567, 785, 514/943

[56] References Cited

U.S. PATENT DOCUMENTS

| | | | |
|---|---|---|---|
| 4,421,747 | 12/1983 | Ghyczy et al. | 514/78 |
| 4,534,980 | 8/1985 | Itoh et al. | 514/570 |
| 4,559,326 | 12/1985 | Crawford et al. | 514/226.5 |

FOREIGN PATENT DOCUMENTS 64-13020  1/1989  Japan .

OTHER PUBLICATIONS

Suzuki, Chemical Abstract 110:237141z (1989) for JP 63-150221 (Jun. 1988).
Chem. Abstract vol. 111:84132r, Suzuki, JP-89-13020, (1989).
English Abstract of JP-A-59-33211 (1984), Nishikawa.
English translation of the Japanese publication "Progress in Medicine", (vol. 4, No. 7 p. 1412 (1984), T. Kageyama.
T. Higuchi, "Physical Chemical . . . Creams and Ointments", Journal of the Society of Cosmetic Chemists, 11, pp. 85–97 (1960).

*Primary Examiner*—Philip I. Datlow
*Attorney, Agent, or Firm*—Sprung Horn Kramer & Wood

[57] ABSTRACT

An emulsified composition for treating the skin containing diclofenac sodium, a fatty acid and a dialkyl carboxylate, as essential components.

5 Claims, No Drawings

EMULSIFIED EXTERNAL TREATMENT COMPOSITION CONTAINING DICLOFENAC SODIUM

This application is a continuation of application Ser. No. 07/875,573, filed Apr. 27, 1992, now abandoned, which is a continuation of Ser. No. 07/731,376, filed Jul. 16, 1991, now abandoned, which is a continuation of Ser. No. 07/384,238, filed Jul. 21, 1989, now abandoned.

BACKGROUND OF THE INVENTION

1. Field of the Invention

The present invention relates to an emulsified external treatment composition containing diclofenac sodium and having an excellent stability.

2. Description of the Related Art

Diclofenac sodium is an excellent nonsteroidal antiphlogistic analgesic in the form of white crystals or a crystalline powder, is soluble in an alcoholic solvent such as methanol or ethanol, but is not easily solubilized in a polar oil such as ether, chloroform, diethyl phthalate, diethyl adipate, diisopropyl adipate, and diethyl sebacate. Accordingly, as the method of using diclofenac sodium in an external treatment agent, since it is soluble in an alcohol, there is known a gel preparation as in the case of indomethacin (Japanese Unexamined Patent Publication (Kokai) No. 59-76013) or an oily ointment having an improved solubility in an oily base by using a dissolving aid such as propylene glycol, (Japanese Unexamined Patent Publication (Kokai) No. 59-33211). Also, O/W type emulsion bases have been developed (Progress in Medicine, Vol. 4, 1411–1413, 1984), but have a problem of stability of the pharmaceutical preparation, and a satisfactory emulsion base has not been obtained.

When an emulsified external treatment agent containing diclofenac sodium is prepared, it is very difficult to effect emulsification, because diclofenac sodium, although slightly soluble in water, is substantially not soluble in diethyl adipate or diethyl sebacate, and even if emulsification is effected by dissolving it in water while heating, a drawback arises in that diclofenac sodium crystals will be precipitated after a certain time. Although the development of an emulsion base having an excellent texture is desired, an emulsified external treatment agent stably containing diclofenac sodium is not known to date.

SUMMARY OF THE INVENTION

Accordingly, the objects of the present invention are to eliminate the above-mentioned disadvantages of the prior art and to provide an emulsified external treatment composition pharmaceutically stably containing diclofenac sodium.

Other objects and advantages of the present invention will be apparent from the following description.

In accordance with the present invention, there is provided an external treatment composition comprising diclofenac sodium, a fatty acid, and a dialkyl carboxylate, as essential components.

DESCRIPTION OF THE PREFERRED EMBODIMENTS

According to the present invention, by combining diclofenac sodium with a fatty acid which is liquid at normal temperature or room temperature and a lower carboxylic acid diester, and effecting emulsification under specific conditions, a pharmaceutically remarkably stable external treatment composition can be obtained.

The amount of diclofenac sodium formulated in the emulsified external treatment composition according to the present invention is preferably 0.5 to 5.0% by weight, more preferably 1.0 to 3.0% by weight, based on the total weight of the emulsified external treatment composition. If the content of diclofenac sodium is too low, pharmaceutical stabilization may be easily effected, but the pharmacological effect will be undesirably poor. Conversely, if the content is too high, a fatty acid and a dialkyl carboxylate must be used in large amounts, and thus the stability of the emulsified external treatment composition cannot be easily retained.

Examples of the fatty acid to be formulated in the emulsified external treatment composition of the present invention include fatty acids having 6 to 18 carbon atoms which exhibit a liquid state at normal temperature, such as n-heptanoic acid, 2-ethylheptanoic acid, peralgonic acid, caprylic acid, isostearic acid, oleic acid, linoleic acid, and linolenic acid. Particularly preferable representative examples include oleic acid, linolenic acid, and isostearic acid. These fatty acids can be used either alone or as a mixture thereof, and can be formulated at a ratio of 0.5 to 20% by weight, preferably 1.0 to 10% by weight, in the emulsified external treatment composition.

Examples of the dialkyl carboxylate to be formulated in the emulsified external treatment composition include dialkyl adiptates having a total of 12 to 22 carbon atoms, dialkyl pimellate having a total of 13 to 23 carbon atoms, dialkyl suberates having a total of 14 to 24 carbon atoms, dialkyl azelaates having a total of 13 to 21 carbon atoms, dialkyl sebacates having a total of 14 to 22 carbon atoms, and dialkyl phthalates having a total of 12 to 24 carbon atoms, such as diethyl phthalate, dibutyl phthalate, isopropyl myristate, diisopropyl azelaate, diisopropyl adipate, dibutyl adipate, diisobutyl adipate, diethyl sebacate, and dibutyl sebacate. Particularly preferable representative examples are diethyl adipate, diisopropyl adipate, dibutyl adipate, diethyl sebacate, and dibutyl sebacate. These dialkyl carboxylates can be used alone or as a mixture thereof, and preferably are formulated at a ratio of 0.25 to 50% by weight, more preferably 0.5 to 20% by weight, in the emulsified external treatment composition.

To stably formulate diclofenac sodium in the emulsified external treatment composition, a fatty acid alone or a dialkyl carboxylate alone is insufficient, but an extremely stable emulsified external treatment composition can be made for the first time by combining these elements at a mixing ratio by weight of preferably ½ or more, most preferably 1:1 to 5:1, of the dialkyl carboxylate relative to the fatty acid. The dissolved product of these elements with diclofenac sodium can be used as such as the oily base by using petrolatum, lanolin, beeswax, and modified bentonite, but the result is oily and is not preferable from the viewpoint of useability. Also, these oily bases are not preferable pharmaceutically, because the solubility of diclofenac sodium is remarkably dependent on the temperature and is liable to be crystallized at a low temperature, and further, the viscosity and hardness of the base is remarkably varied.

The emulsified external treatment composition of the present invention can be prepared by dissolving diclofenac sodium with a mixture of a fatty acid and a dialkyl carboxylate, and to improve the emulsification stability, by emulsifying the mixture by an addition of an oil component with lower polarity than the fatty acids generally used in cosmetic or external treatment composition, while strongly stirring.

Examples of the oil component to be formulated in the diclofenac containing emulsified external treatment composition are triglycerides such as olive oil, soybean oil, rapeseed oil, coconut oil, and tallow; synthetic ester oils such as oleyl oleate, and isopropyl myristate; liquid paraffins; squalane; and silicone oils.

The amount formulated is not particularly limited, but if too low, the stability of the emulsified composition is poor, and if too high, the solubility of diclofenac sodium is poor. The surfactant to be formulated in the emulsified external treatment composition is preferably a hydrophilic surfactant, which may be either nonionic or ionic, provided that it is a hydrophilic surfactant, and can be used alone or in combination.

Examples of the nonionic surfactant are polyoxyethylene sorbitane fatty acid esters, polyethylene glycol fatty acid esters, polyoxyethylene glycerine fatty acid esters, polyethylene alkyl ethers, polyoxyethylene polyoxypropylene alkyl ethers, polyoxyethylene alkyl phenyl ethers, polyoxyethylene hardened castor oil, polyglycerine fatty acid esters, and sugar esters. Examples of the ionic surfactants are alkyl sulfates, polyoxyethylene alkyl ether sulfates, N-acylamino acids, N-acylamino acid salts, N-acylmethyltauric acid, alkylphosphates, alkylsulfone carboxylates, triethanolamine, diethanolamine, diisopropanolamine, amine salts of lysine, and arginine, which are basic amino acids.

Further, hydrophilic surfactants derived from natural products such as casein, saponin, phospholipid, sugar peptide, alginic acid, soybean protein, and yolk protein, can be used in any desired mixture.

The amount of the hydrophilic surfactant to be formulated in the diclofenac sodium emulsified external treatment composition of the present invention is preferably 0.05 to 20% by weight, more preferably 0.1 to 10% by weight.

If the amount of these hydrophilic surfactants formulated is less than 0.05% by weight, a stable emulsified external composition cannot be obtained. Conversely, if it exceeds 20% by weight, skin irritation may be increased or the percutaneous absorptivity may be worsened.

The diclofenac sodium emulsified external treatment composition according to the present invention can be prepared specifically by the following method.

Diclofenac sodium is dissolved under heating in a fatty acid and a dialkyl carboxylate, and the oil component added to the solution to form an oil phase. On the other hand, an aqueous phase is prepared by adding a humectant such as propylene glycol and the above hydrophilic surfactant. Next, emulsification is effected under high speed stirring while adding the oil phase to the aqueous phase, whereby a diclofenac sodium containing an emulsified external treatment agent is obtained. If desired, some water can be added to assist the high speed stirring emulsification treatment, followed by an addition of the remaining water under stirring. During emulsification in the present invention, a conventional homomixer may be employed, but desirably a pressurized emulsifying machine such as a Manthon Gaulin Homogenizer (manufactured by Manthon Gaulin Co., U.S.A.), or Microfluidizer (manufactured by Micrifluidex Corporation, U.S.A.), or an emulsifying machine such as Ultrasonic homogenizer, or Polytron emulsifying machine (Type RT 45/50 KINEMATICA GbbH, made in Switzerland), can be used to perform the emulsifying treatment at a high shearing force, whereby an emulsified external treatment agent having a finer particle size can be obtained. The external treatment agent containing diclofenac sodium of the present invention comprises fine emulsified particles having diameters of 1 μm or less, preferably 0.5 μm or less, on an average, has an excellent physical stability with a lapse of time, and can withstand temperatures of −5° to 50° C. The emulsified external treatment agent containing diclofenac sodium according to the present invention is liquid, but can be thickened by an addition of a water-soluble polymer such as Carbopol, bentonite, or a higher alcohol, to be made into a form such as a milky lotion or cream.

EXAMPLES

The present invention will now be further illustrated by, but is by no means limited to, the following Examples, wherein all percentages are expressed on a weight basis unless otherwise noted. Measurement of the particle size of the emulsified external agent containing diclofenac sodium was conducted by using a NICOMP Model 270 (manufactured by HIACROYCO).

Example 1 (Milky lotion)

| | Example 1 (Milky lotion) | |
|---|---|---|
| (1) | Diclofenac sodium | 1.0% |
| (2) | Purified oleic acid (Extraolein 90 (manufactured by Nisshin Seiyu) | 2.0 |
| (3) | Diisopropyl adipate | 2.0 |
| (4) | ODO (octyldecyl octyltriglyceride) | 4.0 |
| (5) | Glycerine | 5.0 |
| (6) | 1,3-Butylene glycol | 7.0 |
| (7) | POE (60 mole) hardened castor oil | 1.5 |
| (8) | Preservative | q.s. |
| (9) | Carboxyvinyl polymer | 0.2 |
| (10) | Potassium hydroxide | 0.14 |
| (11) | Purified water | Balance |

Preparation method

To the component (1) were successively added the components (2) and (3), and the whole heated to about 70° C. while stirring, to be dissolved therein, and the component (4) was added to the resultant solution, while being cooled to 40° C. to prepare an oil phase. On the other hand, the components (5), (6), and (7) were successively added and dissolved by heating at 40° C., followed by addition of a part of the component (11) to prepare an aqueous phase. Thereafter, while adding the aqueous phase to the oil phase, a preliminary emulsification was conducted by using a homomixer at 10,000 rotations for 2 minutes, and a further treatment was conducted by using a Manthon Gaulin homogenizer at 250 kg/cm$^2$, 6 times, to obtain an emulsion with a particle size of 0.2 μm. Further, the component (9) was dissolved in the remainder of the component (11), neutralized with an addition of the component (10), and then the emulsion previously obtained was added under stirring to obtain the desired emulsified external treatment composition containing diclofenac sodium.

The emulsified external treatment composition containing diclofenac sodium was found to be very stable for 6 months or longer in tests at respective temperatures of −5° C., 0° C., 40° C., and room temperature without decomposition of the diclofenac sodium and without a coalescence of particles or crystal precipitation of diclofenac sodium. Also, the texture was excellent.

Example 2 (Cream)

Example 2 (Cream)

| | | |
|---|---|---|
| (1) | Diclofenac sodium | 3.0% |
| (2) | Isostearic acid | 6.0 |
| (3) | Isopropyl adipate | 10.0 |
| (4) | Castor oil | 27.0 |
| (5) | ODO (octyldecyl octyltriglyceride) | 25.0 |
| (6) | Ethyl paraben | 0.1 |
| (7) | Glycerine | 5.0 |
| (8) | Dipropylene glycol | 7.0 |
| (9) | POE (55 mole) stearic acid | 4.5 |
| (10) | Purified water | Balance |

Preparation method

To the component (1) the components (2) and (3) were successively added and heated to about 70° C. while stirring to be dissolved therein, and to the resultant solution were added the components (4), (5), and (6), while being cooled to 50° C. to prepare an oil phase. The components (7) and (8) were added to the component (9) and dissolved by heating, followed by an addition of a part of the component (10) to prepare an aqueous phase. Thereafter, by using an Agihomomixer (manufactured by Kabushiki Kaisha Tokush Kikako), the oil phase was gradually added into the aqueous phase to obtain the desired creamy emulsified external treatment composition containing diclofenac sodium with particle sizes of 0.5 μm or less.

The emulsified external treatment composition containing diclofenac sodium was found to be very stable for 3 months or longer in tests at respective temperatures of −5° C., 0° C., 50° C., and room temperature, without decomposition of diclofenac sodium and without coalescence of the particles or crystal precipitation of diclofenac sodium. Also, the texture was excellent.

Example 3 (Lotion type)

| | | |
|---|---|---|
| (1) | Diclofenac sodium | 0.5% |
| (2) | Purified oleic acid (Extraolein 90, Nisshin Seiyu) | 0.5 |
| (3) | Diisopropyl adipate | 1.5 |
| (4) | Soybean oil | 1.0 |
| (5) | Decaglycerine monoleate | 0.4 |
| (6) | Hydrogenated lecithin | 0.1 |
| (7) | Glycerine | 1.5 |
| (8) | Propylene glycol | 1.0 |
| (9) | Benzalkonium chloride | 0.1 |
| (10) | Purified water | Balance |

The components (1), (2), and (3) were successively added and dissolved by heating, followed by addition of the component (4), and the temperature was controlled to 45° C. to form an oil phase. On the other hand, the components (5) and (6) were added to the components (8) and (7) and a part of the component (10) and dissolved by heating, and the solution obtained was controlled to a temperature of 45° C. and gradually added to the aqueous phase to effect preliminary emulsification. Then the mixture was passed 10 times through a Microfluidizer under a treatment condition of 350 kg/cm², and after the component (9) was dissolved in the remainder of the component (10), the Microfluidizer treated product was added under stirring to obtain an emulsified external treatment composition containing diclofenac with a particle size of 0.2 μm or less. The emulsified external composition was found to be very stable for 6 months or longer at −5° C. to 40° C. and 3 months or longer at 50° C., without decomposition of the diclofenac sodium and without coalescence of the particles or crystal precipitation of the diclofenac sodium. Also, it was found to have an excellent texture.

Example 4 (Cream)

| | | |
|---|---|---|
| (1) | Diclofenac sodium | 1.0% |
| (2) | Extraolein 90 (Nichiyu) | 2.0 |
| (3) | Diethyl sebacate | 10.0 |
| (4) | ODO (medium chain fatty acid triglyceride) | 2.0 |
| (5) | Liquid paraffin Crystol 172 | 0.5 |
| (6) | Ethyl paraben | 0.1 |
| (7) | Potassium Stearate | 0.4 |
| (8) | 1,3-Butylene glycol | 10.0 |
| (9) | Glycerine | 5.0 |
| (10) | Buffering agent | q.s. |
| (11) | Bentonite | 5.0 |
| (12) | Cetyl alcohol | 0.5 |
| (13) | Purified water | Balance |

Preparation method

To the component (1) were successively added the components (2) and (3) and dissolved by heating. Further, the components (4), (5), and (6) were added and dissolved by heating, and then the solution was controlled to a temperature of 40° C. to form an oily phase. On the other hand, the component (7) was dissolved by heating in the components (8) and (9) and a part of the component (12) and the solution was controlled to a temperature of 40° C. to form an aqueous phase. Preliminary emulsification was effected by adding the oil phase to the aqueous phase while carrying out the homomixer treatment, and a further treatment was conducted by a Manthon Gaulin homogenizer at 350 kg/cm², 6 times, to obtain a uniform liquid emulsified composition with a particle size of 0.2 μm or less. On the other hand, the components (12), (11), and (10) were successively added to the remainder of the component (13) and dispersed under a strong shearing force by Despar, and then the liquid emulsified external treatment composition was gradually added under stirring to obtain a creamy emulsified external composition containing diclofenac sodium. The emulsified external treatment composition was found to have a good texture, with no deterioration in appearance at temperature tests at to 5° C., 0° C., 40° C., and room temperature for 6 months. Also there was no decomposition of the diclofenac sodium, coalescence of particles, or crystal precipitation of the diclofenac sodium, and thus the stability was found to be very good. Also, the stability in the cycle test at 50° C. (5° to 45° C., 2 cycles/day) was found to be good for 3 months or longer.

I claim:

1. An emulsified external treatment composition, which comprises, based on the total weight of the composition, (i) an active component consisting essentially of diclofenac sodium, in 0.5 to 5.0%, (ii) 0.5 to 20% of a fatty acid, which is liquid at room temperature, (iii) 0.25 to 50% of a dialkyl carboxylate, the weight ratio of the dialkyl carboxylate to the fatty acid being 1/1 to 5/1, (iv) an oil component, (v) a hydrophilic surfactant and (vi) a humectant.

2. A composition as claimed in claim 1, wherein the fatty acid is at least one component selected from the group consisting of fatty acids having 6 to 18 carbon atoms which exhibit a liquid state at room temperature.

3. A composition as claimed in claim 1, wherein the dialkyl carboxylate is at least one component selected from the group consisting of dialkyl adipates having a total of 12 to 22 carbon atoms, dialkyl pimellate having a total of 13 to 23 carbon atoms, dialkyl suberates having a total of 14 to 24 carbon atoms, dialkyl azelaates having a total of 13 to 21 carbon atoms, dialkyl sebacates having a total of 14 to 22 carbon atoms and dialkyl phthalates having a total of 12 to 24 carbon atoms.

4. A composition according to claim 1, consisting of (i), (ii), (iii), (iv), (v) and (vi).

5. A process for stably emulsifying diclofenac sodium in an emulsified external treatment composition which comprises:

a) dissolving under heat 0.5 to 5% by weight of diclofenac sodium in a solution of 0.5 to 20% by weight of a fatty acid which is liquid at room temperature and 0.25 to 50% by weight of dialkyl carboxylate all based upon the total weight of the composition, the weight ratio of the dialkyl carboxylate to the fatty acid being 1/1 to 5/1;

b) adding to the solution formed in step a), an oil component followed by cooling to produce an oil phase;

c) forming an aqueous phase by mixing together at least one hydrophilic surfactant and at least one humectant; and d) emulsifying said oil phase and aqueous phase by adding the oil phase to the aqueous phase under high speed stirring.

\* \* \* \* \*